United States Patent [19]

Buck et al.

[11] Patent Number: 5,234,812

[45] Date of Patent: Aug. 10, 1993

[54] METHOD FOR SEQUENTIAL DETERMINATION OF AN ANALYTE IN A FLUID SAMPLE USING A THIRD RECEPTOR

[75] Inventors: Harvey Buck; Fern DeLaCroix; Hans Berger, all of Indianapolis, Ind.

[73] Assignee: Boehringer Mannheim Corporation, Indianapolis, Ind.

[21] Appl. No.: 697,095

[22] Filed: May 8, 1991

Related U.S. Application Data

[62] Division of Ser. No. 281,410, Dec. 8, 1988, Pat. No. 5,079,174.

[51] Int. Cl.$^5$ .................. C12Q 1/00; G01N 33/535
[52] U.S. Cl. ........................... 435/7.5; 435/7.9; 435/7.92; 435/7.94; 435/7.95; 436/512; 436/518; 436/540; 436/543; 436/538
[58] Field of Search ............ 435/7.94, 7.95, 7.92, 435/7.9, 7.5; 436/518, 512, 540, 543, 538

[56] References Cited

U.S. PATENT DOCUMENTS

| | | | |
|---|---|---|---|
| 4,185,084 | 1/1980 | Mochida et al. | 435/7.94 |
| 4,471,058 | 9/1984 | Smith et al. | 435/7.4 |
| 4,615,983 | 10/1986 | Koyama | 436/514 |
| 4,624,930 | 11/1986 | Tanswell et al. | 435/7.94 |
| 4,738,823 | 4/1988 | Engelmann | 422/56 |
| 4,839,297 | 6/1989 | Freitag et al. | 436/170 |
| 5,061,619 | 10/1991 | Wilson et al. | 435/7.94 |

OTHER PUBLICATIONS

Oellerich, J. Clin. Chem. Biochem. 18: 197–199 (1980).

*Primary Examiner*—Sam Rosen
*Attorney, Agent, or Firm*—Felfe & Lynch

[57] ABSTRACT

The invention relates to an assay for determining an analyte in a fluid sample. Three receptors are used, with formation of a quaternary or four member complex. One of the receptors is bound to a solid phase, and binds to complexes of another receptor and the analyte. A third receptor is labelled, and it, too, binds analyte. The invention also involves the use of a displacement solution to wash fluid sample from solid phase after the first portion of the quaternary complex forms, i.e., prior to binding with the labelled receptor.

12 Claims, 1 Drawing Sheet

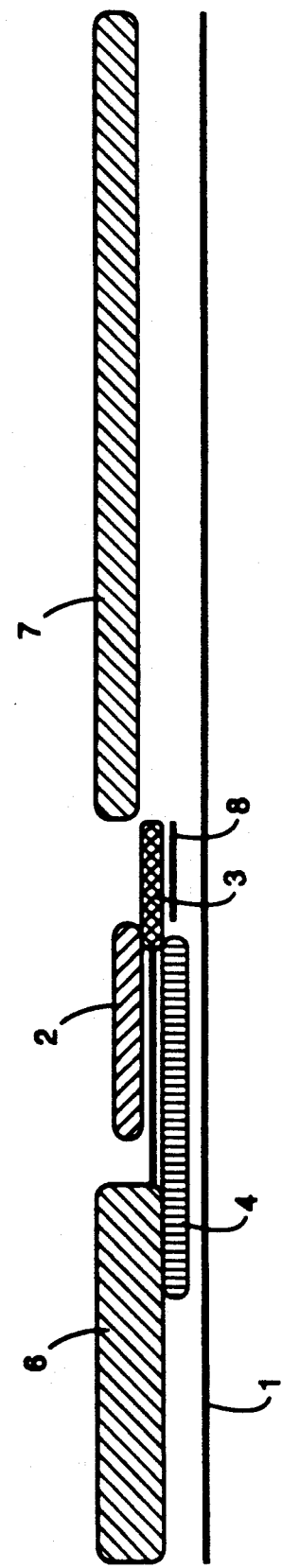
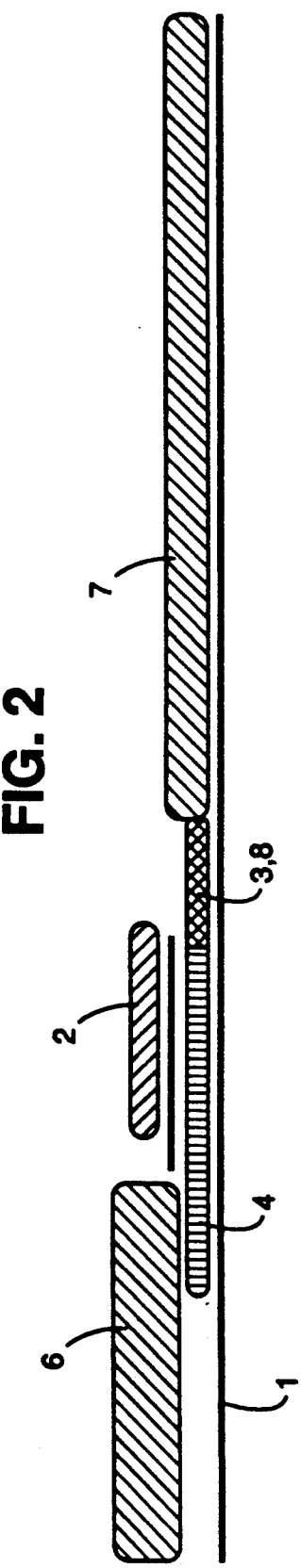

METHOD FOR SEQUENTIAL DETERMINATION OF AN ANALYTE IN A FLUID SAMPLE USING A THIRD RECEPTOR

This application is a divisional of U.S. patent application Ser. No. 07/281,410, filed Dec. 8, 1988 and now U.S. Pat. No. 5,079,174.

FIELD OF THE INVENTION

This invention relates to an apparatus useful in determining an analyte in a fluid sample. It also relates to a method for determining an analyte in a sample, using a four member, or "quaternary" complex involving the analyte, a whole monoclonal antibody which binds to said analyte, a labeled monoclonal antibody Fab fragment which also binds to the analyte, where both of these are obtained from the same animal species, and a solid phase bound antibody which may or may not be monoclonal, which binds to the Fc portion of a monoclonal antibody but not to its Fab portion.

BACKGROUND AND PRIOR ART

The formation of sandwiches of antigen and antibody and their use in immunoassays has been in use for over fifteen years. The art has seen two distinct trends in the field. The earliest trend was toward the formation of ternary complexes, i.e., complexes of the form - $Ab_1$-$Ag$-$Ab_2^*$, where $Ab_2^*$ carries some label. The later trend is to multiple component systems, usually quaternary, but sometimes involving five or more components. The prior art discussion maintains this distinction.

I. Ternary Complex Formation

The patent literature contains many examples of inventions in this area. An early example of such an assay may be found in Schuurs, et al., U.S. Pat. No. 3,654,090 (1972), which is useful not only as historical background, but for an understanding of some of the key facets of this field.

Schuurs, et al. teaches detection of an antigen using a solid phase bound antibody against one epitope, or binding site, of the antigen, as well as a soluble, enzyme labeled antibody which binds with a second portion of the antigen. The method disclosed in Schuurs, et al. involves determination of the enzyme label after the sandwich between bound antibody, antigen, and labeled antibody forms. This is accomplished either in the solid phase, or in the liquid phase, by addition of a substrate for the enzyme label. Usually, the enzyme-substrate reaction produces a color or change in color, which can be recognized in "yes-no" tests, or quantitated where the amount of substance present is to be determined.

Absent from Schuurs, et al. is any discussion of monoclonal antibodies or antibody fragments and this is not surprising since Schuurs, et al. was filed in 1968, and issued in 1972, i.e., much earlier than the breakthroughs in hybridoma technology which occurred following the development of the Köhler-Milstein method for producing monoclonal antibodies.

Schuurs, et al. received another patent in 1974, U.S. Pat. No. 3,791,932, again directed to sandwich assays. This patent describes a so-called "forward" sandwich immunoassay. This type of assay calls for a specific order of steps, i.e., the sample being tested is first contacted with the insoluble binding partner and the reaction between these two is allowed to proceed to completion. The solid phase complexes are removed from the solution, and the second binding partner, containing an enzyme label, is then added to the solid phase. Following binding to the complex, the enzyme level is determined, following the standard techniques referred to, supra. Again, there is no mention of monoclonal antibodies or antibody fragments.

Ling, in U.S. Pat. No. 3,867,517 (1975), taught that enzymes were not the only label which could be used in sandwich assays. This patent describes a forward sandwich assay using as the label a radioactive antibody. The radioactive label was $^{125}I$, a standard radioisotope. Radiolabelling of antibodies is a standard technique, but assumes the presence of the proper amino acids in the antibody molecule for binding of the radioactive iodine. Otherwise, the label does not hold.

Schuurs, et al., received yet another patent in 1977, U.S. Pat. No. 4,016,043. This patent claims to teach a simpler version of rudimentary sandwich assays. It teaches using an insoluble component of an antigen-antibody reaction and a labeled sample of the same component. This method assumes that the antigen being detected has two identical epitopic sites. Further, the use of two identical receptors precludes the use of "simultaneous" assays, which are discussed infra. The consequences of this is that the Schuurs '043 assay can take as long as 60 hours to complete. In the clinical or diagnostic laboratory, the large amount of time requires is unacceptable.

Piasio, et al., U.S. Pat. No. 4,098,876 (1978) taught a "reverse" sandwich assay. This patent is important because it showed, first, that the component being determined could be bound to the soluble, labeled antibody first, and the immobilized antibody second. It was also an improvement in that a washing step was eliminated, which meant that time was saved in performing the assay. Piasio, et al. teach that their assay could, ideally, be completed in under one-half hour. This paradigmatic system was not realized in their examples, but the time was substantially less than the 60 hours for Schuurs, et al., discussed supra. A significant drawback of the method is that it requires enormous amounts of immobilized antibody.

Niswender, U.S. Pat. No. 4,048,298 (1977), is actually not a sandwich assay, but shows an invention where an immobilized antibody was used to bind another antibody. This patent teaches an interesting variation on older competitive immunoassays. Niswender contacts a solid phase bound antibody with the sample being assayed as well as a second, radiolabeled antibody which binds to the first, but not to the component being determined. The effect of this is to allow the investigator to determine substance present by determining how much radiolabeled antibody binds to the solid phase.

This patent shows that antibodies can bind to other antibodies rather than just antigens. This property is important in more recent assays, some of which are discussed infra.

Schwarzberg, U.S. Pat. No. 4,235,689 (1980) recognized that antibodies possess two distinct portions, the Fc portion, or "constant" region, and the Fab portion, which is the part of the antibody which binds to an epitopic site. Schwarzberg prepared complexes of labeled Fab fragments bound to a ligand, such as a polypeptide. This complex is then used in so-called "competitive" assays. No solid phase binding, or sandwich assays, are described.

Jeong, et al., U.S. Pat. No. 4,244,940 (1981) teaches a "simultaneous" sandwich immunoassay. Such an assay requires an antigen with different epitopic sites, because two different antibodies or receptors must be used, for the reasons elaborated upon supra.

With Jeong, et al., it will be seen that by 1981 the state of the art in this field did teach forward, reverse, and simultaneous assay, always with ternary complexes (i.e., complexes of three species) being formed. The art had begun to see the use of Fab fragments as "linker" molecules (Schwarzberg), but they had not been used as an essential part of an immunoassay system, nor had monoclonal antibodies been used.

Both of these ideas were taught in patents which issued in 1983. David, et al., U.S. Pat. No. 4,376,110 (1983), overcame a prejudice in the art that monoclonal antibodies were not "sticky" enough, i.e., possessed insufficient affinity for use in sandwich assays. David, et al., taught that all three forms of ternary sandwich assays could be performed with monoclonal antibodies, as long as they both had affinities of at least $10^8$ liters/mole. Moussebois, et al., in U.S. Pat. No. 4,397,060 (1983), taught an agglutination assay could be performed using Fab fragments bound to a solid support. This patent shows, yet again, that Fab fragments were not being considered as partners of immunoassays, even though monoclonal antibodies themselves were now being used.

Gallati, et al., U.S. Pat. No. 4,467,031 (1984) taught a specific sandwich assay, for determination of carcinoembryonic antigen (CEA). The key feature of this invention was the use of different salt concentrations to improve complex formation. It is a "forward" sandwich assay, as the term is defined herein, and discusses the possibility of two monoclonal antibodies being used in the assay. It will be seen that this, too, is a ternary complex, and that an Fab fragment is not being used.

Woods, et al., U.S. Pat. No. 4,469,787 (1984) teaches a sandwich assay which requires the binding of a label to the Fc portion of a second antibody. The label is not directly attached to the second antibody, rather, Woods et al. assert invention in that the label is bound to the Fc portion of the antibody after the ternary complex is formed. This is done so as to prevent interference between the label and the immobilized first antibody.

U.S. Pat. No. 4,486,530 (1984), which issued to David, et al., and is a continuation in part of U.S. Pat. No. 4,376,110, discussed supra, again teaches ternary monoclonal antibody sandwiches and their detection. This patent adds to the art by showing that sandwich assays can be performed in homogeneous phase, i.e., without phase separation. This is performed by labeling the monoclonal antibody components of the ternary complexes with labels which do not react unless brought together by the "glue" of a multiepitopic antigen.

Carro, et al., U.S. Pat. No. 4,522,922 (1985) combine sandwich assays with an older form of immunoassay, the so-called "precipitation" test. This invention teaches formation of a ternary sandwich, followed by addition of a precipitating agent to precipitate the complex out of solution. This is a radioimmunoassay, which employs polyclonal antisera.

The most recent patents in the field show modifications on the basic sandwich principle. Petska, in U.S. Pat. No. 4,623,621 (1986), teaches that an oligomeric protein can be measured by using a solid phase bound monoclonal antibody which is specific for an epitope present once on the repeating protein portion of the molecule. After solid phase binding, a second sample of the same monoclonal antibody, only labeled, is bound. Again, a ternary complex is formed, only with whole antibodies, and simultaneous assaying is not possible.

II. Multiple Member Complex Formation

The earliest example of a quaternary system is exhibited by U.S. Pat. No. 4,343,896, which issued to Wolters, et al. This patent which is based on a disclosure filed in 1976, teaches the solid phase bound complex $Ab_1\text{-}Ab_2\text{-}Ag\text{-}Ab_3^*$. A crucial limitation in the Wolters patent is that $Ab_2$ and $Ab_3^*$ come from different animal species. The reason for this is because $Ab_1$ has to be directed against the constant region, i.e., "Fc" portion of $Ab_2$. All antibodies of a particular immunological class which come from the same animal species will have identical Fc portions. If $Ab_2$ and $Ab_3$ were from the same animal species, the art taught that not only would $Ab_1\text{-}Ab_2\text{-}Ag\text{-}Ab_3^*$ but one one would also obtain $Ab_1\text{-}Ab_3^*$, both of which would bind to the solid phase, causing interference and incorrect results.

Axen, et al., U.S. Pat. No. 4,469,796 (1984) teaches that more than three components may be involved in an immune reaction, but the only four part complex taught is a solid phase bound complex of $Ag\text{-}Ab_1\text{-}Ab_2\text{-}Ab_3^*$. It is noteworthy that in the description of reactants given at column 1, lines 41-60, Axen, et al. never mentions Fab fragments.

Tanswell, et al., U.S. Pat. No. 4,624,930 (1986) teaches four component complexes wherein a first and third receptor in solution bind to the antigen while a second solid phase antibody binds to the first antibody. Tanswell's teaching is generic to the use of a double antibody system and it does not specifically disclose monoclonal antibodies.

Forrest, et al., U.S. Pat. No. 4,659,678 (1987) goes beyond the four part binding discussed supra, and actually forms a pentavalent complex of antibody-hapten-antibody-antigen-antibody. The tail end of the complex is a radioactively labeled antibody. At least one antibody must be a monoclonal antibody.

Forrest, et al. detail at some length the advantages and disadvantages of multi-member complex forming assays. The solution to the problems set forth at, e.g., column 2, lines 1-5, is to use a solid phase bound mAb, to bind a complex of $Ab\text{-}Ag\text{-}Fab^*$. The only time a solid phase bound mAb is used to bind the complex $mAb_2\text{-}Ag\text{-}Fab^*$, however, Forrest requires that the $mAb_2$ be bound to another antigen, so that the solid phase complex $mAb_1\text{-}Ag_2\text{-}mAb_2\text{-}Ag_1\text{-}Fab^*$ is formed. It must be understood in this context, however, that "$Ag_2$" actually stands for a linking agent, as $mAb_2$ cannot possess binding sites for two different Ags.

In U.S. Pat. No. 4,891,313 and assigned to the assignees of this application, a device and method are described involving quaternary immunoassays. The device is adapted for using the method, which involves contacting an analyte with a pair of receptors, specifically a labeled monoclonal antibody or labeled fragment (e.g., a Fab or Fab' fragment), a second non-labeled monoclonal antibody, and a solid phase bound receptor, which may be an antibody. The two non-solid phase bound antibodies are from the same animal species. These components are combined to form a quaternary "sandwich" structure.

Quaternary structures provide increased sensitivity; however, there is problem present in the quaternary assay, and this disclosure is directed to solution of that problem.

In performing immunoassays one generally works with body fluid samples, such as blood or urine. These are not ideal systems for immunological analysis, as they contain native substances which interfere with the desired binding between the analye and the labeled receptor or "conjugate". See, in this regard, Boscato, et al., Clin. Chem. 34(11): 27-33 (1988); European Patent Specification 83 869. This interference results in skewed, and false results in diagnosis, pregnancy determination, etc.

Prior art devices available for performing immunoassays do not address this problem. These devices are configured so that the labeled receptor is introduced to the medium containing the analyte to be determined while the interfering substances are still present.

It is an object of the invention to provide an apparatus useful in performing assays where the problem of interference from substances native to the sample being analyzed is eliminated.

It is a further object of the invention to provide a method for carrying out diagnostic assays of the type described herein, without interference by native substances.

How these and other objects of the invention are accomplished will be determined from the disclosure which follows.

BRIEF DESCRIPTION OF THE FIGURES

FIG. 1 shows one embodiment of a device in accordance with this invention.

FIG. 2 shows a second embodiment of a device in accordance with this invention.

The device of this invention is an apparatus which is adapted for determining an analyte in a sample with the elimination of interference by other components of the sample. The device is specifically adapted for use in quaternary sandwich immunoassays.

Reference to the figures will be helpful in understanding both the device and the method of this invention. Referring to FIG. 1, the device includes a support 1, which is inert, and which serves basically to contain the other features of the apparatus. A first zone 2 is provided, which may also be described as the "first wick" of the invention. This first zone 2 is adapted for reception of the sample. This first zone 2 contains a first receptor, such as an antibody, or a biotinylated antibody, which specifically binds to the analyte being determined. This first receptor is not solid phase bound, and is removable from the first zone 2 when sample is added. It will be referred to as the "capture" receptor.

The first zone 2 is in at least partial fluid contact with a second zone 3, which does contain a solid phase bound receptor, or "matrix" receptor. This solid phase bound receptor may be any of a number of substances, such as an antibody, protein A, an avidin/streptavidin system and so forth. This receptor must, however, bind to the capture receptor of the first zone.

The device also includes a third zone 4, and it is this third zone 4 which defines the invention. Third zone 4 contains the conjugate receptor, such as a labeled antibody or antibody fragment. It is positioned relative to the first zone 2 so that when sample is applied to the first zone, the sample does not contact the third zone 4. Thus, first zone 2 and third zone 4 are separated by a liquid impermeable barrier 5, which prevents the conjugate of third zone 4 from diffusing into the first zone. The apparatus shows a liquid application means 6 which is in partial fluid contact with the third zone 4. Fluid application means 6 is shown to be separate from first zone 2, although this is not essential. This liquid application means 6 permits application of a liquid which does dislodge the conjugate, since the sample does not.

When an assay is being performed, a sample liquid to be analyzed is added to first zone 2. Any capture receptor which binds to the analyte to be determined will complex to the analyte, forming a receptor-analyte complex which is contained in the liquid. Liquids, by their nature, flow, so the complex containing liquid will continue to move through the apparatus.

The liquid then moves into the second zone 3, which contains the matrix receptor. This receptor binds to the capture receptor previously introduced in the first zone, and immobilizes both complexes and uncomplexed first receptor.

In prior art devices, by this point the labelled conjugate has been introduced. Either the labelled conjugate is introduced in the first zone, or in the solid phase zone. In both cases, the conjugate is introduced while the sample liquid together with its native, interfering substance, is present.

In the inventive device, however, such is not the case, The impermeable barrier 5 precludes contact of the sample with third zone "4", which contains the conjugate. Thus, the sample reaches the matrix without the conjugate, and solid phase complexing occurs.

Introduction of the conjugate then takes place, via one of several alternative schema. It is one option, for example, to introduce to sample application zone 2 a "wash", such as a buffer, distilled water, or a running solution. This wash takes the same path as does the sample, but its normal flowability, and its relative inertness result in the sample liquid being dislodged from the matrix, without any interference with the solid phase bound components. Once this is accomplished, one may, e.g., introduce a solution to liquid application means 6. This liquid solution enters third zone 4, and carries the conjugate into second zone 3, where it binds with the analyte, without any interference from the native substances, which, of course have now been removed.

While the wash solution is an option, it is not the only way to accomplish the removal of the sample solution. If one omits the washing step, it has been found that the front of the conjugate containing solution will also "push" the liquid sample being assayed through the device before the conjugate arrives in the second zone. Thus, while it is important to get the liquid sample further down the device, there are several ways to do this.

Once the conjugate has contacted the second zone 3 and flowed therefrom, measurement of the label in the conjugate is required. Measurement is possible via many different processes. Various labels are known which, de facto, produce a detectable signal. Examples of these include metallic particles, such as gold, or materials which, without further interaction, give off a detectable signal, such as fluorescent, radioactive, or chemiluscent materials.

Also envisioned as labels are those materials which react with others to produce the signal, be it colorimetric, fluorescent, and so forth. One exemplary type of label system well known in the art is the "enzyme-substrate" system. In these systems the label is, e.g., an enzyme which reacts with a substrate. The reaction produces a product with a distinct color, change in color, or some other observable property.

When the label is one which inherently produces a signal, it is of course unnecessary to provide a means for introducing a reactant, such as a substrate, to the label. Thus the following discussion relates to those systems where a label is used which requires a reactant to produce a signal. None of the specifically disclosed embodiments are necessary in the device, but they exemplify various ways to bring the label and reactant together.

FIG. 1 shows an option where there is provided a feature 8 which contains a reactant or substrate apart from the matrix 3, while FIG. 2 shows a configuration where the reactant or substrate and matrix are "merged".

The apparatus does not, however, need a substrate diffusion zone, as substrate may be added after the complexing reactions have taken place in their entirety. Substrate application may take place, e.g., by pressing down a structure containing the substrate onto the second zone, or by applying it to the first zone in the liquid application means after complexing has taken place, using a device such as the one described in, e.g., U.S. Pat. No. 4,665,023, FIGS. 1-4, the disclosure of which is incorporated by reference.

The materials used to construct the device of this invention may include many different substances. The zones should be liquid absoptive and possess good capillarity. Examples of materials which may be used include bibulous paper, nitrocellulose paper, sponges, polymeric films, etc. Both fibrous and non-fibrous materials can be used.

As has been alluded to, supra, the various receptors may be a number of materials. In one embodiment the conjugate is a Fab or Fab' fragment of a monoclonal antibody carrying an enzyme label, and the capture receptor is a second whole monoclonal antibody derived from the same species as the conjugate example. Other possible receptors include polyclonal antibodies. The matrix receptor, or solid-phase bound receptor is immobilized via any of the stand means of doing so, such as by cyanogen bromide fixation. The immobilized receptor is preferably an antibody which binds to the Fc portion of the capture antibody, but can be another substance as well, such as protein A, or biotin when the capture antibody has an avidin molecule attached thereto.

Review of this discussion will show that the invention also provides a method for determining an analyte, involving contacting the analyte to a first receptor with formation of complexes therebetween followed by contacting the complexes with a second, solid phase bound receptor. This is followed by binding the third receptor, the conjugate, to the solid phase bound complex. Determining bound or unbound conjugate permits one to assay for the analyte.

DETAILED DESCRIPTION OF PREFERRED EMBODIMENTS

Experiments were performed comparing the apparatus and method of the invention described herein to the apparatus and method described in U.S. Pat. No. 4,891,313.

Two devices were prepared in which most of the components were identical. Specifically, the liquid application means "6" for both devices was a piece of viscose sponge cloth (Kalle, Wiesbaden), cut to 3.0 cm×0.6 cm. Second zone 3 was constructed from a piece of 3512 paper (Schleicher & Schull), which was activated using cyanogen bromide. Sheep anti-mouse Fc antibodies were coupled to the paper, and it was cut to 1.2 cm×0.6 cm. Barrier foil 5 was a 1.0 cm×0.6 cm piece of double-sided adhesive tape (3 m). Waste zone 9 was constructed from a 5. cm×0.6 cm piece of D-28 paper (Whatman).

The devices differed, however, in the construction of first zone 2 and the material impregnated in the third zone 4. Specifically, using the invention described herein, the first zone 2 was a piece of 4210 paper (Kalff) cut to 1.6 cm×0.6 cm, which had impregnated therein 10 ul of a solution of 1 ug of monooclonal antibody to hCG in 0.3% Tween 20 phosphate buffered saline, pH 7.2). The device following U.S. Pat. No. 4,891,313 was impregnated, in contrast to the invention, with a 10 ul solution containing 1 ug of the same monoclonal antibody, but also 0.2U of a conjugate of a Fab fragment of a second monoclonal antibody to hCG conjugated to beta galactosidase, and 0.1% bovine serum albumin. In the invention, the third zone was a piece of 4210 paper cut to 2.5 cm×0.6 cm. A first solution was impregnated on one portion of the second zone, and contained 10 ul of 10% polyvinyl alcohol (Mowiol 4-88, Hoechst), and 0.4 mg of the beta galactosidase substrate methoxy naphthol galactoside (1:1 mix of DMSO and water). Adjacent to the portion of the zone impregnated with the substrate a second solution (10 ul) was impregnated which contained 0.3 U of a conjugate of an Fab portion of monoclonal antibody to hCG conjugated to beta galactosidase, and 20 ug of phenyl-ethyl-thiogalactoside, in a solution of PBS/BSA/Tween. The second galactoside is a beta galactosidase inhibitor.

It is important to note that, in the invention the two solution listed supra are impregnated in the second zone such that, when dried, they are adjacent to each other but do not touch.

In the device following U.S. Pat. No. 4,891,313, the second zone was the same size as in the invention, but was impregnated only with the 4-methoxy-naphthol galactoside solution referred to supra.

To summarize, then, the differences in the device can be summarized by the following Table:

TABLE

|  | Invention | Prior Art |
| --- | --- | --- |
| First Zone | contains one antibody | contains two antibodies, one labelled, and an inhibitor |
| Second Zone | First portion: substrate Second portion: second antibody and inhibitor Portions not contacting each other | contains only label substrate |

The devices were then assemblied onto a white polyester backing sheet using double sided adhesives. Construction of the components into test strips followed standard techniques well known in the art, and for that reason details are not given here.

Assays were then run on both sets of strips, using a control system containing 0 mIU/ml of hCG, and one containing 250 mIU/ml. Additionally a running solution was prepared containing 50 mmol/l sodium phospate; 0.03% Tween 20; 150 mmol/l NaCl; 2 mmol/l NaBO$_3$ (sodium perborate, a peroxidase substrate); and 10 U/ml horseradish peroxidase.

In performing the assays, 150 ul of the sample was applied to the first zone, followed by application of 850 ul of running solution to application point 6. Color development was then observed in the third zone. The expected color is a dark blue, produced by reaction of the enzyme substrate and the beta galactosidase.

The results of the assays were evaluated using a Mac-Beth Reflectance Spectrometer, and the ΔE value for the test areas relative to a plain white paper strip are recorded.

|  | Prior Art | Invention |
|---|---|---|
| hCG concentration |  |  |
| 0 mIU/ml | 10 | 10 |
| 250 mIU/ml | 20 | 30 |

In these units, a difference of 1.0 is sanely discernable, a difference of 2.0 clearly discernable. The difference in values, especially for the sample containing 250 mIU/ml, shows how effective the device and method described herein is in eliminating interference in the assay. The signal generated in response to analyte is much clearer, stronger, and more accurate.

It will be understood that the specification and examples are illustrative but not limitative of the present invention and that our embodiments within the spirit and scope of the invention will suggest themselves to those skilled in the art.

We claim:

1. Method for determining an analyte in a liquid sample comprising sequentially contacting said sample with a first receptor which specifically binds said analyte under conditions favoring formation of a complex between said first receptor and said analyte in said solution, contacting said complex containing solution with a solid phase bound second receptor which specifically binds to said first receptor under conditions favoring binding of said complex to said solid phase, displacing said liquid sample from said solid phase with a displacing solution, and contacting said solid phase bound complex with a third labelled receptor which binds to said analyte but not to said first or second receptor to bind said third receptor thereto, and determining said label in either bound or unbound to said complex as an indication of analyte in said sample.

2. Method of claim 1, wherein said displacement solution contains said third receptor.

3. Method of claim 1, wherein said displacement solution is a wash solution.

4. Method of claim 1, wherein at least one of said first, second, and third receptors is an antibody.

5. Method of claim 1, wherein said second receptor is protein A.

6. Method of claim 1, wherein said second receptor is avidin/streptavidin and said first receptor is biotinylated.

7. Method of claim 1, wherein said second receptor is an antibody.

8. Method of claim 1, wherein said third receptor is a Fab or F(ab')$_2$ fragment 9. Method of claim 4, wherein said antibody is monoclonal.

10. Method of claim 8, wherein said fragment is a fragment of a monoclonal antibody.

11. Method of claim 1, wherein said label is chromophoric, fluorescent or radioactive.

12. Method of claim 1, wherein said label is an enzyme.

* * * * *